United States Patent [19]

Saphakkul

[11] Patent Number: 4,964,874
[45] Date of Patent: Oct. 23, 1990

[54] HAIR TREATMENT PRODUCT

[75] Inventor: Fongchan Saphakkul, Bangkok, Thailand

[73] Assignee: Unilever Patent Holdings B.V., Rotterdam, Netherlands

[21] Appl. No.: 258,738

[22] Filed: Oct. 17, 1988

[30] Foreign Application Priority Data

Oct. 15, 1987 [GB] United Kingdom ............... 8724254

[51] Int. Cl.$^5$ ........................ A61K 7/13; A61K 7/06
[52] U.S. Cl. ...................................... 8/429; 8/405; 8/426; 8/435; 424/70
[58] Field of Search .................. 8/405, 406, 426, 429, 8/435; 424/70

[56] References Cited

FOREIGN PATENT DOCUMENTS 2168082 6/1986 United Kingdom .

Primary Examiner—Paul Lieberman
Assistant Examiner—John F. McNally
Attorney, Agent, or Firm—Cushman, Darby & Cushman

[57] ABSTRACT

An aqueous hair conditioner product comprises a cationic surfactant, a fatty alcohol having an alkyl group with from 8 to 22 carbon atoms, a basic dye, and a neutral dye, the cationic surfactant being present in the form of a disperse lamellar liquid crystal phase, and the weight ratio of basic dye to neutral dye being from 1:20 to 1:2.

12 Claims, No Drawings

HAIR TREATMENT PRODUCT

FIELD OF INVENTION

The invention relates to a product for treating keratinous fibres and more particularly to a product for conditioning and dyeing hair in order to darken it. For the sake of clarity, the following description is concerned with the dyeing of human hair, although it is to be understood that the product according to the invention can be employed in the treatment of other keratinous fibres, such as wool or animal fur, in order to dye them or to impart other benefits such as conditioning to them.

BACKGROUND AND PRIOR ART

As human hair becomes grey, for example, due to ageing or following a psychosomatic disorder, or is bleached due to excessive exposure to sunlight, a need can arise on the part of the consumer for a treatment to darken or to restore the color of the hair to its former appearance. Although it is possible to darken hair with a single treatment using, for example, an oxidative dye, the consumer usually prefers a gradual darkening treatment, so that the return to the original shade is not dramatic and therefore not noticeable to casual observer.

Direct dyes have been employed by Beecham Group PLC as described in GB No. 2 168 082 for dyeing hair using a composition containing, in addition to the dye, a cationic surfactant and a liquid carrier. These dyes are stated to include anthraquinone, azo, nitro, basic, triarylmethane or disperse dyes or any combination thereof.

In our attempts to develop a hair dye system which not only satisfies the desire of the consumer to obtain gradual darkening of the hair following repeated treatments over a period of weeks or months, while providing a rapid, even color change following each treatment, we have assessed the suitability for this purpose of a range of direct dyes, including basic dyes and neutral dyes. We were also concerned to provide a product that could be applied to the hair in the manner normally employed for shampoos and conditioners, without the need to wear gloves to avoid unacceptable staining of the hands with the dye.

Our experiments have shown that when using certain basic dyes, color uptake by the hair is rapid in that only a short treatment time of a few minutes is needed to achieve a moderate darkening of the hair, but that hand staining can occur to an unacceptable extent when the concentration of basic dye is sufficiently high to achieve adequate dyeing under these conditions.

We have also shown that when using certain neutral dyes, uniform dye coverage can be obtained, but the colour uptake by the hair is slower than with basic dyes, in that a longer treatment time is needed to achieve a moderate darkening of the hair. Furthermore, little or no hand staining is experienced with neutral dyes at concentrations sufficient to give adequate dyeing which is usually higher than that of the basic dye.

Accordingly, by using a product containing both a basic dye and a neutral dye, at carefully controlled concentrations, together with a cationic surfactant, which is present in the form of a disperse lamellar liquid crystal phase, we have discovered that it is possible to achieve rapid, uniform dyeing of the hair to a degree which satisfies the needs of the consumer desiring gradual darkening over a course of treatment as explained earlier, the product being suitable for application to the hair without the need to employ gloves.

Additionally, the cationic surfactant imparts a conditioning benefit to the hair which is retained after rinsing with water hair treated with this product.

DEFINITION OF THE INVENTION

Accordingly, the invention provides an aqueous hair conditioner product which comprises:
(i) from 0.1 to 5% by weight of a cationic surfactant,
(ii) from 0.1 to 5% by weight of a fatty alcohol having an alkyl group with from 8 to 22 carbon atoms,
(iii) from 0.001 to 0.5% by weight of a basic dye, and
(iv) from 0.001 to 5% by weight of a neutral dye;
the cationic surfactant being present in the form of a disperse lamellar liquid crystal phase, and the weight ratio of basic dye to neutral dye being from 1:20 to 1:2, preferably from 1:10 to 1:2.

DISCLOSURE OF THE INVENTION

The disperse lamellar liquid crystal phase

The hair conditioner product of the invention which is also capable of imparting color to the hair comprises, in an aqueous medium, a cationic surfactant and a fatty alcohol, the cationic surfactant being present in the form of a disperse lamellar liquid crystal phase.

(i) The cationic surfactant

Examples of suitable cationic surfactants include quaternary ammonium chlorides and bromides having at least one long chain ($C_{12-22}$) alkyl group or at least one aryl group. Specific surfactants which are suitable include oleyl dimethylbenzylammonium chloride, cetyl trimethylammonium chloride, cetyl trimethylammonium bromide, methyl bis [2-hydroxyethyl]oleylammonium chloride, stearyl trimethylammonium chloride, and distearyl dimethylammonium chloride.

The amount by weight of cationic surfactant to be employed in the composition according to the invention is from 0.1 to 5%, preferably from 0.2 to 3% by weight of the product.

(ii) The fatty alcohol

The cationic surfactant of the hair rinse conditioner of the invention is present in the aqueous compositions as a disperse lamellar liquid crystal phase rather than in micellar form, as it would normally occur in a simple aqueous solution. The production of a disperse lamellar liquid crystal phase is most conveniently effected by the inclusion of a fatty alcohol having an alkyl group with from 8 to 22, preferably from 16 to 20 carbon atoms. Examples of suitable fatty alcohols include cetyl alcohol and stearyl alcohol, which themselves also contribute to the overall conditioning properties of the compositions.

The amount by weight of such fatty alcohols form from 0.1 to 5% by weight of the product, the amount being sufficient to convert the cationic surfactant to the disperse lamellar liquid crystal phase.

The weight ratio of cationic surfactant to fatty alcohol is usually from 1 10 to 10:1, preferably from 1:4 to 4:1 and ideally from 1 1 to 1:4.

The basic dye

The hair conditioner product of the invention comprises one or more basic dyes.

Examples of suitable basic dyes include basic anthraquinone dyes, especially those containing a dialkylaminoalkylamino (DAAA) group. Specific examples include the following:

3-[(4-amino-6-bromo-5,8-dihydro-1-hydroxy-8-imino-5-oxo-2naphthalenyl)amino]-N,N,N-trimethylbenzenaminium chloride
  Trade name: Arianor Steel Blue
  Colour group: Basic blue 99
  CI Number: 56059
[8-[(p-aminophenyl)azo]-7-hydroxy-2-naphthyl]trimethylammonium chloride
  Trade name: Arianor Mahogany
  Colour group: Basic brown 16
  CI Number: 12250
[8[(4-amino-2-N-nitrophenyl)azo]-7-hydroxy-2-naphthyl]trimethylammonium chloride
  Trade name: Arianor Sienna Brown
  Colour group: Basic brown 17
  CI Number: 12251
[8[(0-methoxyphenyl)azo]-7-hydroxy-2-naphthyl]trimethylammonium chloride
  Trade name: Arianor Madder Red
  Colour group: Basic red 76
  CI Number: 12245
  Trade name: Arianor Straw Yellow
  Colour group: Basic yellow 57
  CI Number: 12719
  Trade name: Astra Blue 3R
  Colour group: Basic blue 52
  Trade name: Astrazon Red BL-N
  Colour group: Basic red 45
  Trade name: Astrazon Golden Yellow GLD
  Colour group: Basic orange 29
  Trade name: Astrazon Golden Yellow GRL
  Colour group: Basic yellow 29

The amount by weight of the basic dye to be employed in the product according to the invention is from 0.001 to 0.5%, preferably from 0.01 to 0.1% by weight of the product.

The neutral dye

The hair conditioner product of the invention also comprises one or more neutral dyes.

Examples of suitable neutral dyes include neutral anthraquinone dyes and nitro dyes.

Specific examples of neutral anthraquinone dyes include the following:
1-amino-4-methylamino-9,10-anthracenedione
  Trade name: Celliton Violet 6B
  Colour group: Disperse Violet 4
1,4,5,8-tetraamino-9,10-anthracenedione
  Trade name: Celliton Blue Extra
  Colour group: Disperse Blue 1
1,4-diamino-9,10-anthracenedione
  Trade name: Celliton Red Violet RN
  Colour group: Disperse Violet 1
1,4-diamino-5-nitro-9,10-anthracenedione
  Trade name: Palanil Violet 3B
  Colour group: Disperse Violet 8

Specific examples of neutral nitro dyes include the following:
$N^1,N^4,N^4$-tris (2-hydroxyethyl-2-nitro-4-phenylenediamine)
  Trade name: Fourrine BDN
  Colour group: HC Blue 2
4-nitro-0-aminophenol
2-nitrophenylenediamine The amount of neutral dye to be employed in the product according to the invention is generally from 0.001 to 5%, preferably from 0.01 to 1% by weight of the product.

Water

The hair conditioner product according to the invention is aqueous and accordingly contains water which can be present in one or more of the other ingredients of the product, such as the cationic surfactant or dye solution, or it can be added separately.

The amount of water present will form from 10 to 99%, preferably from 20 to 95% by weight of the product.

Hair conditioner adjuncts

The hair conditioner product according to the invention can also optionally comprise other materials that are conventionally employed in such products including, thickening and suspending agents, opacifiers, pearlescent agents, sequestrants, colour stabilising agents, perfumes, preservatives, glycols and other dye soublisers. In addition to water, the product can also comprise other liquids to form a liquid vehicle for the surfactant, fatty alcohol and dyes. Examples of such liquids include ethanol and isopropanol.

pH

The pH of the composition of the hair conditioner product according to the invention can be from 2 to 9, preferably from 2.5 to 7. If necessary, the pH can be adjusted using conventional agents.

Preparation of the hair conditioner product

The invention also provides a process for the preparation of a hair conditioner product which is capable of imparting color to the hair, which process comprises:
(a) admixing a cationic surfactant in an aqueous liquid vehicle with a fatty alcohol having an alkyl group with from 8 to 22 carbon atoms at a temperature above the melting point of the fatty alcohol, this temperature being not less than about 50° C., preferably from 50° to 80° and most preferably from 60° to 80° C., to form on cooling a solution containing the surfactant in a disperse lamellar liquid crystal phase;
(b) admixing one or more basic dyes and one or more neutral dyes with the solution; and
(c) adjusting the pH value of the hair conditioner product so obtained as necessary to a value of from 2 to 9, preferably from 2.5 to 7.

Optionally, a thickening agent can be dissolved or dispersed in the product at any convenient stage in the process in order to provide the hair conditioning product with a desired viscosity to suit the consumer.

Further hair conditioning adjuncts can also be added at any convenient stage in the process, preferably before final pH adjustment.

Method of treatment of hair

The invention also provides a method for treating non-human or human hair comprising the step of applying an effective amount of the hair conditioner product according to the invention to the hair. According to a preferred method, 10 g to 30 g of the product are applied to the hair, preferably whilst still wet following shampooing. The product is allowed to remain in contact with the hair for about 2 minutes and is then rinsed from the hair with warm water (25° to 40° C.) and finally dried.

MEASUREMENT OF HAIR COLOUR

In order to assess the color of hair dyed with products according to the invention, the reflectance spectra of hair switches were measured from 400-700 nm in a Micromatch spectrophotometer in the absence of ultraviolet light. Colour difference analysis from these data were made using computer programs.

Small switches of blond hair, each 10 cm in length and weighing 0.5 g were accommodated in the spectrophotometer using a holder with a narrow slit. Only switches in good condition with well aligned fibres were used. Due to the itinerant variance of hair, each switch was repositioned at least four times in the holder for multiple readings. An average value was used in calculating the colour intensity.

The use of standards in the colour analysis of hair is necessary as the perception of colour cannot be measured directly and is dependent on:
(i) the visible reflectance spectrum ($R[\lambda]$),
(ii) the spectral energy distribution of the light source ($S[\lambda]$), and
(iii) the spectral sensitivity of the eye ($x[\lambda]$).

For consistency and comparability these last two need to be defined as standards.

The colour space is defined by the tristimulus values X, Y and Z; thus:

$$X = K \left\{ \sum_{400}^{700} R[\lambda] \cdot S[\lambda] \cdot x[\lambda] \right\}$$

and similarly for Y and Z. K is a factor which ensures that the maximum value of Y for any illuminant spectral distribution is 100.

Values of $S[\lambda]$ and of $x[\lambda]$ have been determined and are an integral part of the CIE 1976 standards. In the experiments to be described later in this specification, the illuminant $D_{65}$ for the 10° observer was used.

The values X, Y and Z give a non-uniform colour space with respect to colour perception. It is necessary, therefore, to transform them into the approximately uniform colour space given by L, A and B, as defined by the CIELAB 76 formulae. These values are expressed in rectangular coordinates.

The L value is a measure of the brightness of the sample on a grey scale from white to black. The A and B values are measures of the colour where;
+A is red
−A is green
+B is yellow
−B is blue The difference between two samples in the CIELAB space, usually a standard, is given by $$\Delta E = [(\Delta L)^2 + (\Delta A)^2 + (\Delta B)^2]$$

The product according to the invention, when employed in the dyeing of hair according to the procedure described herein using blond hair, will provide a colour intensity ($\Delta E$) value preferably of at least 25. Ideally, the colour intensity ($\Delta E$) value obtained is at least 30.

EXAMPLES

The invention is illustrated by the following Examples:

EXAMPLE 1

A hair conditioning product according to the invention capable of darkening hair contained the following ingredients:

|  | % w/w |
| --- | --- |
| Cetyl trimethyl ammonium chloride | 1 |
| Cetostearyl alcohol | 2.75 |
| Coconut monoethanolamide | 1 |
| Paraffin wax | 1 |
| Basic dyes: | |
| Arianor Steel Blue | 0.15 |
| Arianor Mahogany | 0.03 |
| Neutral dyes: | |
| Fourrine BDN 100% | 0.15 |
| Celliton Violet 6B | 0.2 |
| Perfume | 0.7 |
| Preservative | 0.25 |
| Minor Ingredients | 2 |
| Water | up to 100 |

Hair dyeing properties

The in vitro method for assessing dye uptake by human hair is as follows:

A hair switch (0.25 g) is treated twice for 1 minute each time with 0.25 g of water and 0.05 g of shampoo comprising by weight 12% sodium lauryl 2-ether sulphate and 2% coconut diethanolamide, rinsing with water for 30 seconds with water and dried.

The switch is then treated with water (0.25 g) and hair colouring conditioner (0.05 g) for 5 minutes at 45° C., rinsed for 30 seconds with water and finally dried.

In a typical experiment, 10 of the above cycles are completed.

The intensity of the dark brown colour obtained was determined using the Micromatch spectrophotometer as described herein and the following CIELAB values were obtained.

L = 49
A = 1
B = 2

From these values, the $\Delta E$ value was calculated as 30. This confirmed that a strong, intense dark brown colour was obtained.

Hair Conditioning Properties

The above hair conditioner product was compared in a wet combing test with a commercially available opaque cream rinse conditioner based on the combination of a cationic surfactant (cetyltrimethylammonium bromide) and a fatty alcohol (ceto/stearyl alcohol). The wet combing test was carried out in the following manner.

A hair switch (8 g) was washed with a surfactant solution (16% monoethanolamine lauryl sulphate) (MLS) in two stages, this solution being referred to hereafter as the surfactant base. In the first application 0.5 ml of the surfactant base was applied to the wetted hair, the switch lathered for 30 seconds and, after leaving for a further 20 seconds, the hair was rinsed with water. This was repeated but using 0.4 ml of the surfactant base. After rinsing and removing excess water, the hair was combed until free of tangles with a comb which was in association with an instrument which measured the total combing time (TCT). The TCT value after treatment with the surfactant base is T1. The hair switch was then treated with 0.5 ml of the hair conditioner test product according to the invention which was massaged into the hair for 30 seconds. After leaving for 60 seconds the hair switch was rinsed with water. After removing excess water, the switch was again combed free of tangles to give a TCT value of T2. The combing time after treatment with the test hair conditioner product expressed as a percentage of that after treatment with the surfactant base is $T2/T1 \times 100$. The procedure was carried out on two other hair switches and the average of the percentage values for the three switches was taken as the wet combing value for the test product. Thus, the more effective the product, the lower the wet combing value. A different set of three switches was used for each test product. The wet combing values given in this example were each obtained by the same operator. The reproducibility of the wet combing values was found to be ±2 units.

The results are given in the following table:

| Test Product | Wet Combing Value |
| --- | --- |
| Conditioner of Example 1 | 18 |
| Commercially available opaque cream rinse conditioner | 20 |

These results show that the conditioner of the invention is at least equivalent to the commercially available opaque cream rinse conditioner.

The results have been confirmed by an in-vivo evaluation in the hair salon. The product of the invention was judged to be similar to the commercially available opaque conditioner with no significant differences between the various attributes being compared which also included hair gloss, static charge and ease of styling. This confirmed that the product of Example 1 had excellent conditioning properties as well as the ability to darken hair to a desired extent.

EXAMPLE 2

A hair conditioning product according to the invention capable of darkening hair contained the following ingredients:

| | % w/w |
| --- | --- |
| Cetyl trimethyl ammonium chloride | 1.0 |
| Cetostearyl alcohol | 1.5 |
| Preservative | 0.25 |
| Arianor Steel Blue | 0.05 |
| Arianor Mahogany | 0.05 |
| Celliton Violet | 0.3 |
| 4 nitro-0-amino-phenol | 0.1 |
| Hydroxypropyl Guar | 1.0 |
| Water | to 100.0 |
| pH = 4 | |

After 10 treatments in accordance with the method described in Example 1, the following CIELAB colour coordinates were obtained.

| L | A | B |
| --- | --- | --- |
| 52 | 4 | 7 |

From these values, the $\Delta E$ value was calculated as 26. This confirmed that a mid brown color was obtained.

I claim:
1. An aqueous hair conditioner product comprising:
  (i) from 0.1 to 5% by weight of a cationic surfactant,
  (ii) from 0.1 to 5% by weight of a fatty alcohol having an alkyl group with from 8 to 22 carbon atoms,
  (iii) from 0.001 to 0.5% by weight of a basic dye, and
  (iv) from 0.001 to 5% by weight of a neutral dye;
the cationic surfactant being present in the form of a disperse lamellar liquid crystal phase, and the weight ratio of basic dye to neutral dye being from 1:20 to 1:2.

2. A product according to claim 1, wherein the cationic surfactant is selected from the group consisting of quaternary ammonium chlorides and bromides having at least one alkyl group with from 12 to 22 carbon atoms, or at least one aryl group.

3. A product according to claim 1, wherein the cationic surfactant forms from 0.2 to 3% by weight of the product.

4. A product according to claim 1, wherein the fatty alcohol is selected from the group consisting of cetyl alcohol, stearyl alcohol and mixtures thereof 5. A product according to claim 1, wherein the weight ratio of cationic surfactant to fatty alcohol is from 1:4 to 4:1.

6. A product according to claim 1, wherein the basic dye is selected from the group consisting of Arianor Steel Blue, Arianor Mahogany, Arianor Sienna Brown, Arianor Madder Red, Arianor Straw Yellow, Astra Blue 3R, Astrazon Red BL-N, Astrazon Golden Yellow GLD, Astrazon Golden Yellow GRL and mixtures thereof 7. A product according to claim 1, wherein the basic dye forms from 0.01 to 0.1% by weight of the product.

8. A product according to claim 1, wherein the neutral dye is selected from the group consisting of Celliton Violet 6B, Celliton Blue Extra, Celliton Red Violet RN, Palanil Violet 3B, Fourrine BDN, 4-nitro-0-aminophenol, 2-nitrophenylenediamine and mixtures thereof.

9. A product according to claim 1, wherein weight ratio of basic dye to neutral dye is from 1:10 to 1:2.

10. A product according to claim 1, wherein the neutral dye forms from 0.01 to 1% by weight of the product 11. A product according to claim 1, comprising from 10 to 99% by weight of water.

12. A method of darkening hair, wherein the hair is treated with a product according to claim 1.